(12) United States Patent
Kim et al.

(10) Patent No.: US 11,681,219 B2
(45) Date of Patent: Jun. 20, 2023

(54) RESIST COMPOSITION

(71) Applicant: SAMSUNG ELECTRONICS CO., LTD., Suwon-si (KR)

(72) Inventors: Yechan Kim, Hwaseong-si (KR); Su Min Kim, Suwon-si (KR); Ju-Young Kim, Hwaseong-si (KR); Jinjoo Kim, Seoul (KR); Hyunwoo Kim, Seongnam-si (KR); Juhyeon Park, Suwon-si (KR); Hyunji Song, Suwon-si (KR); Songse Yi, Seoul (KR); Suk Koo Hong, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 276 days.

(21) Appl. No.: 16/991,281

(22) Filed: Aug. 12, 2020

(65) Prior Publication Data
US 2021/0263411 A1 Aug. 26, 2021

(30) Foreign Application Priority Data
Feb. 6, 2020 (KR) .................. 10-2020-0014504

(51) Int. Cl.
G03F 7/004 (2006.01)
C08L 35/00 (2006.01)
(Continued)

(52) U.S. Cl.
CPC .......... G03F 7/0045 (2013.01); C07C 381/12 (2013.01); C08L 25/06 (2013.01); C08L 35/00 (2013.01)

(58) Field of Classification Search
CPC ..... G03F 7/0045; C07C 13/15; C07C 13/465; C07C 13/567; C07C 23/40
See application file for complete search history.

(56) References Cited

U.S. PATENT DOCUMENTS 5,569,784 A 10/1996 Watanabe et al.
6,171,755 B1 * 1/2001 Elian ...................... G03F 7/405
430/296
(Continued)

FOREIGN PATENT DOCUMENTS

JP 2018-199781 A 12/2018
KR 10-0881883 B1 2/2009
(Continued)

OTHER PUBLICATIONS

Odedra, J. Org. Chem, 72, 3289-3292 (2007).
(Continued)

Primary Examiner — Chanceity N Robinson
Assistant Examiner — Anna Malloy
(74) Attorney, Agent, or Firm — Lee IP Law, P.C.

(57) ABSTRACT

A resist composition including a polymer; and a compound represented by Formula 1,

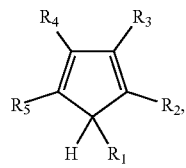

[Formula 1]

in Formula 1, $R_1$ is hydrogen, a halogen, an alkyl group having 1 to 7 carbon atoms, a carbonyl group having 1 to 7 carbon atoms, an ester group having 1 to 7 carbon atoms, an acetal group having 1 to 7 carbon atoms, an alkoxy group having 1 to 7 carbon atoms, an ether group having 1 to 7 carbon atoms, or a group repre-
(Continued)

sented by Formula R, and $R_2$, $R_3$, $R_4$ and $R_5$ are hydrogen, a halogen, an alkyl group having 1 to 7 carbon atoms, an ester group having 1 to 7 carbon atoms, an acetal group having 1 to 7 carbon atoms, an alkoxy group having 1 to 7 carbon atoms, or an ether group having 1 to 7 carbon atoms,

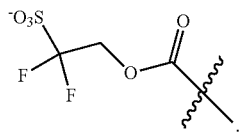

[Formula R]

18 Claims, 5 Drawing Sheets

(51) Int. Cl.
*C07C 381/12* (2006.01)
*C08L 25/06* (2006.01)

(56) References Cited

U.S. PATENT DOCUMENTS

| | | |
|---|---|---|
| 6,855,476 B2 | 2/2005 | Ferreira et al. |
| 7,220,532 B2 | 5/2007 | Takata et al. |
| 7,871,751 B2 | 1/2011 | Echigo et al. |
| 7,901,865 B2 | 3/2011 | Hirayama et al. |
| 8,367,298 B2 | 2/2013 | Ichikawa et al. |
| 8,574,817 B2 | 11/2013 | Hatakeyama et al. |
| 8,735,048 B2 | 5/2014 | Inasaki et al. |
| 9,052,589 B2 | 6/2015 | Kramer et al. |
| 9,182,668 B2 | 11/2015 | Hasegawa et al. |
| 9,316,915 B2 | 4/2016 | Hatakeyama et al. |
| 9,625,813 B2 | 4/2017 | Tsuchimura et al. |
| 10,101,654 B2 | 10/2018 | Hatakeyama et al. |
| 2004/0191672 A1* | 9/2004 | Oguro .................. G03F 7/0392 430/283.1 |
| 2005/0233242 A1* | 10/2005 | Yamanaka ............ G03F 7/0045 430/270.1 |
| 2010/0113818 A1* | 5/2010 | Oh ....................... C07D 311/84 560/111 |
| 2017/0192353 A1 | 7/2017 | Aqad et al. |
| 2019/0112265 A1 | 4/2019 | Masuyama et al. |
| 2019/0113844 A1 | 4/2019 | Hatakeyama et al. |

FOREIGN PATENT DOCUMENTS

| | | |
|---|---|---|
| KR | 10-1145088 B1 | 5/2012 |
| KR | 10-1772733 B1 | 8/2017 |

OTHER PUBLICATIONS

Miyamoto et al., Org. Letters, vol. 10, No. 14, 2975-2978 (2008).
Deng et al., Org. Letters, vol. 9, No. 25, 5207-5210 (2007).
Xu et al., J. Org. Chem, vol. 80, 7779-7784 (2015).
Liu et al., Angew. Chem. Int. Ed., vol. 49, 2909-2912 (2010).

\* cited by examiner

RESIST COMPOSITION

CROSS-REFERENCE TO RELATED APPLICATION

Korean Patent Application No. 10-2020-0014504, filed on Feb. 6, 2020, in the Korean Intellectual Property Office, and entitled: "Resist Composition," is incorporated by reference herein in its entirety.

BACKGROUND

1. Field

Embodiments relate to a resist composition.

2. Description of the Related Art

In order to fulfill excellent performance and low costs for consumers, the integration degree and the improvement of reliability of semiconductor devices may be increased. With the increase of the integration degree of semiconductor devices, finer patterning may be performed during the manufacturing process of the semiconductor devices. The patterning of a target layer to be etched may be performed by an exposure process and a developing process using a photoresist layer.

SUMMARY

The embodiments may be realized by providing a resist composition including a polymer; and a compound represented by Formula 1,

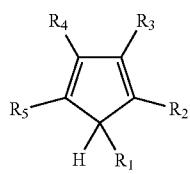

[Formula 1]

wherein, in Formula 1, $R_1$ is hydrogen, a halogen, a substituted or unsubstituted alkyl group having 1 to 7 carbon atoms, a substituted or unsubstituted carbonyl group having 1 to 7 carbon atoms, a substituted or unsubstituted ester group having 1 to 7 carbon atoms, a substituted or unsubstituted acetal group having 1 to 7 carbon atoms, a substituted or unsubstituted alkoxy group having 1 to 7 carbon atoms, a substituted or unsubstituted ether group having 1 to 7 carbon atoms, or a group represented by Formula R, and $R_2$, $R_3$, $R_4$ and $R_5$ are each independently hydrogen, a halogen, a substituted or unsubstituted alkyl group having 1 to 7 carbon atoms, a substituted or unsubstituted ester group having 1 to 7 carbon atoms, a substituted or unsubstituted acetal group having 1 to 7 carbon atoms, a substituted or unsubstituted alkoxy group having 1 to 7 carbon atoms, or a substituted or unsubstituted ether group having 1 to 7 carbon atoms, $R_2$, $R_3$, $R_4$ and $R_5$ being separate or adjacent ones thereof are combined to form an aromatic ring having 3 to 20 carbon atoms, provided that in Formula 1, provided that $R_1$ is a group represented by Formula R, or $R_2$ and $R_3$ or $R_4$ and $R_5$ are combined with each other to form an aromatic ring having 3 to 20 carbon atoms,

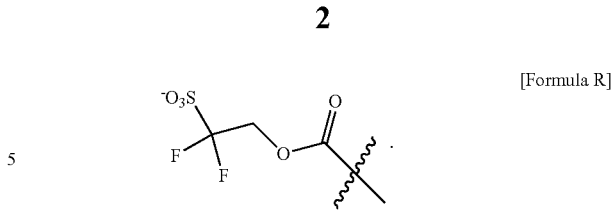

[Formula R]

The embodiments may be realized by providing a composition including a polymer; a quencher; and a compound represented by Formula 1A,

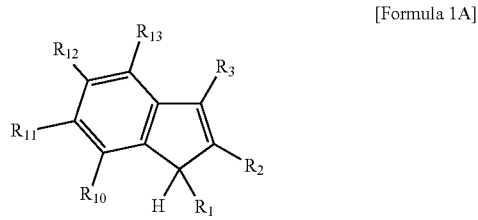

[Formula 1A]

wherein, in Formula 1A, $R_1$, $R_{10}$, $R_{11}$, $R_{12}$ and $R_{13}$ are each independently hydrogen, a halogen, a substituted or unsubstituted alkyl group having 1 to 7 carbon atoms, a substituted or unsubstituted carbonyl group having 1 to 7 carbon atoms, a substituted or unsubstituted ester group having 1 to 7 carbon atoms, a substituted or unsubstituted acetal group having 1 to 7 carbon atoms, a substituted or unsubstituted alkoxy group having 1 to 7 carbon atoms, a substituted or unsubstituted ether group having 1 to 7 carbon atoms, or $-COO(CH_2)CF_2SO_3^-$, and $R_2$ and $R_3$ are each independently hydrogen, a halogen, a substituted or unsubstituted alkyl group having 1 to 7 carbon atoms, a substituted or unsubstituted ester group having 1 to 7 carbon atoms, a substituted or unsubstituted acetal group having 1 to 7 carbon atoms, a substituted or unsubstituted alkoxy group having 1 to 7 carbon atoms, or a substituted or unsubstituted ether group having 1 to 7 carbon atoms, $R_2$ and $R_3$ being separate or combined with each other to form an aromatic ring having 3 to 20 carbon atoms.

The embodiments may be realized by providing a composition including a polymer; a quencher; and a photo-acid generator represented by Formula A-1,

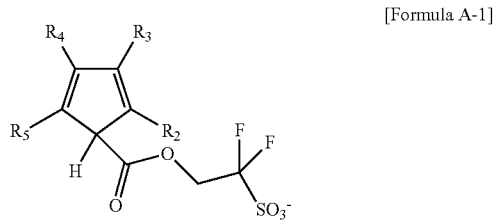

[Formula A-1]

in Formula A-1, $R_2$, $R_3$, $R_4$ and $R_5$ are each independently hydrogen, a halogen, a substituted or unsubstituted alkyl group having 1 to 7 carbon atoms, a substituted or unsubstituted ester group having 1 to 7 carbon atoms, an acetal group having 1 to 7 carbon atoms, an alkoxy group having 1 to 7 carbon atoms, or an ether group having 1 to 7 carbon atoms; $R_2$, $R_3$, $R_4$ and $R_5$ being separate or adjacent ones thereof are combined to form an aromatic ring having 3 to 20 carbon atoms.

BRIEF DESCRIPTION OF THE DRAWINGS

Features will be apparent to those of skill in the art by describing in detail exemplary embodiments with reference to the attached drawings in which.

DETAILED DESCRIPTION

Figure 1A:
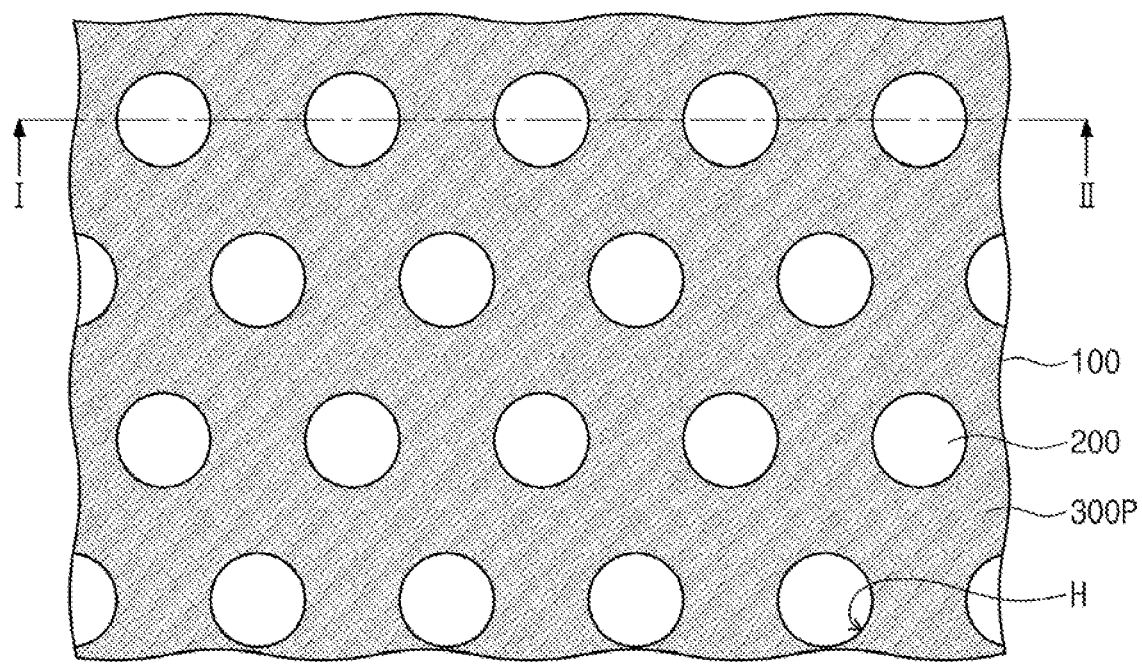
FIG. 1A is a plan view showing a resist pattern according to embodiments.

In the description, the carbonyl group may be a substituted or unsubstituted carbonyl group, unless otherwise defined. The ester group may be a substituted or unsubstituted ester group. The acetal group may be a substituted or unsubstituted acetal group. The alkoxy group may be a substituted or unsubstituted alkoxy group. The ether group may be a substituted or unsubstituted ether group.

The description of forming a ring via the combination with an adjacent group may mean forming a substituted or unsubstituted hydrocarbon ring, or a substituted or unsubstituted heterocycle via the combination with an adjacent group. The hydrocarbon ring includes an aliphatic hydrocarbon ring and an aromatic hydrocarbon ring. The heterocycle includes an aliphatic heterocycle and an aromatic heterocycle. The ring formed by the combination with an adjacent group may be a monocyclic ring or a polycyclic ring. In addition, the ring formed via the combination with an adjacent group may be combined with another ring to form a spiro structure.

In the description, the term "adjacent group" may mean a substituent substituted for an atom which is directly combined with an atom substituted with a corresponding substituent, another substituent substituted for an atom which is substituted with a corresponding substituent, or a substituent sterically positioned at the nearest position to a corresponding substituent. For example, in 1,2-dimethylbenzene, two methyl groups may be interpreted as "adjacent groups" to each other, and in 1,1-diethylcyclopentene, two ethyl groups may be interpreted as "adjacent groups" to each other.

In the description, the alkyl group may be a linear alkyl group, a branched alkyl group, or a cyclic alkyl group. The alkyl group may include a primary alkyl, a secondary alkyl, and a tertiary alkyl. The carbon number of the alkyl group is not specifically limited, but may be an alkyl group having 1 to 7 carbon atoms, particularly, an alkyl group having 1 to 5 carbon atoms.

In the description, the alkyl groups of the alkylsulfonate group, alkylthio group, alkylsulfoxy group, alkylcarbonyl group, alkylester group, alkylether group, and alkyl acetal group are the same as the examples of the aforementioned alkyl groups.

In the description, the halogen atom may include fluorine, chlorine, iodine, and/or bromine.

As used herein,

"―|―"

means a connected or bonding position.

In the chemical formula in the description, if a chemical bond is not drawn at a position requiring a chemical bond, it may mean that a hydrogen atom is bonded to the position, unless otherwise defined.

In the description, like reference numerals refer to like elements throughout.

Hereinafter, a composition according to embodiments, a method of forming a pattern using the composition, and a method of manufacturing a semiconductor device will be explained.

According to an embodiment, the composition may be a resist composition. The composition may be used for forming a pattern or for manufacturing a semiconductor device. In an implementation, the resist composition may be used in a patterning process for manufacturing a semiconductor device. The resist composition may be an extreme ultraviolet radiation (EUV) resist composition. The extreme ultraviolet radiation may mean ultraviolet radiation having a wavelength of about 13.0 nm to about 13.9 nm, e.g., a wavelength of about 13.4 nm to about 13.6 nm. The extreme ultraviolet radiation may mean light having energy of about 90 eV to about 95 eV. In an implementation, the resist composition may be used in an exposure process using argon fluoride (hereinafter, ArF) as a light source. The light source using ArF may emit light of a wavelength of about 185 nm to about 200 nm, e.g., a wavelength of about 190 nm to about 195 nm. The resist composition may be a chemically amplified resist type (CAR type) resist composition.

In an implementation, the resist composition may include a compound represented by the following Formula 1.

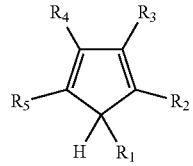

[Formula 1]

In Formula 1, $R_1$ may be or include, e.g., hydrogen, a halogen, a substituted or unsubstituted alkyl group having 1 to 7 carbon atoms, a substituted or unsubstituted carbonyl group having 1 to 7 carbon atoms, a substituted or unsubstituted ester group having 1 to 7 carbon atoms, an acetal group having 1 to 7 carbon atoms, an alkoxy group having 1 to 7 carbon atoms, an ether group having 1 to 7 carbon atoms, or a group represented by the following Formula R. $R_2$, $R_3$, $R_4$ and $R_5$ may each independently be or include, e.g., hydrogen, a halogen, a substituted or unsubstituted alkyl group having 1 to 7 carbon atoms, a substituted or unsubstituted carbonyl group having 1 to 7 carbon atoms, a substituted or unsubstituted ester group having 1 to 7 carbon atoms, an acetal group having 1 to 7 carbon atoms, an alkoxy group having 1 to 7 carbon atoms, or an ether group having 1 to 7 carbon atoms. In an implementation, $R_2$, $R_3$, $R_4$ and $R_5$ may be separate, or adjacent ones thereof may be combined to form an aromatic ring having 3 to 20 carbon atoms. As used herein, the term "or" is not an exclusive term, e.g., "A or B" would include A, B, or A and B.

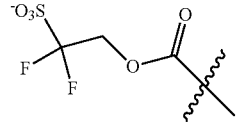

[Formula R]

In an implementation, in Formula 1, $R_1$ may be a group represented by Formula R, or $R_2$ and $R_3$ may be combined with each other to form an aromatic ring having 3 to 20 carbon atoms.

In an implementation, the polymer may be a photoresist material. In an implementation, the polymer may include a polymerization unit represented by Formula 2A and a polymerization unit represented by Formula 2B. The polymerization unit represented by Formula 2B may be connected with the polymerization unit represented by Formula 2A.

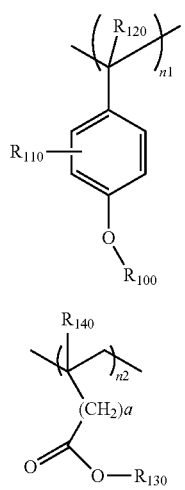

[Formula 2A]

[Formula 2B]

In Formula 2A, $R_{100}$, $R_{110}$ and $R_{120}$ may each independently be or include, e.g., hydrogen or a substituted or unsubstituted alkyl group having 1 to 7 carbon atoms, and "n1" may be an integer of 1 to 1,000,000.

In Formula 2B, $R_{130}$ may be or may include, e.g., a substituted or unsubstituted tertiary alkyl group having 4 to 20 carbon atoms, $R_{140}$ may be or may include, e.g., hydrogen or a substituted or unsubstituted alkyl group having 1 to 7 carbon atoms, "a" may be an integer of 0 to 5, and "n2" may be an integer of 1 to 1,000,000.

In Formula 2A and Formula 2B, n1+n2 may be an integer of 50 to 1,000,001 (e.g., 50 to 1,000,000).

In an implementation, the polymerization unit represented by Formula 2A may include polyhydroxystyrene (PHS) or derivatives thereof.

In an implementation, in Formula 2B, $R_{130}$ may be, e.g., a substituted or unsubstituted cyclic tertiary alkyl group having 4 to 20 carbon atoms.

The resist composition may further include a photo-acid generator. The photo-acid generator may produce hydrogen ions (W) during the exposure process of a resist layer. The photo-acid generator may include a compound represented by the following Formula 3 or a compound represented by the following Formula 4.

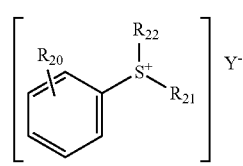

[Formula 3]

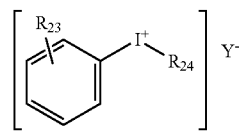

[Formula 4]

In Formula 3, $R_{20}$ may be or may include, e.g., hydrogen, a halogen, or a substituted or unsubstituted alkyl group having 1 to 5 carbon atoms. $R_{21}$ and $R_{22}$ may each independently be or include, e.g., an alkyl group having 1 to 7 carbon atoms or a substituted or unsubstituted aromatic ring group having 4 to 20 carbon atoms. Y may be a conjugate base of a strong acid.

In Formula 4, $R_{23}$ may be or may include, e.g., hydrogen or a substituted or unsubstituted alkyl group having 1 to 5 carbon atoms. $R_{24}$ may be or may include, e.g., an alkyl group having 1 to 7 carbon atoms or a substituted or unsubstituted aromatic ring group having 4 to 20 carbon atoms. Y may be a conjugate base of a strong acid.

In an implementation, the compound represented by Formula 3 may include a compound represented by the following Formula 3A.

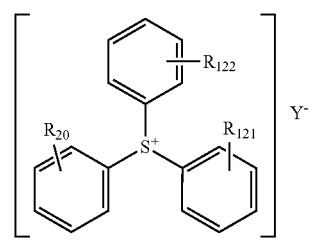

[Formula 3A]

In Formula 3A, $R_{20}$, $R_{121}$ and $R_{122}$ may each independently be or include, e.g., hydrogen, a halogen, or a substituted or unsubstituted alkyl group having 1 to 5 carbon atoms. Y may be the same as defined in Formula 3.

In an implementation, the compound represented by Formula 4 may include a compound represented by the following Formula 4A.

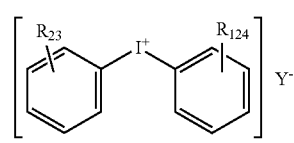

[Formula 4A]

In Formula 4A, $R_{23}$ and $R_{124}$ may each independently be or include, e.g., hydrogen, a halogen, or a substituted or unsubstituted alkyl group having 1 to 5 carbon atoms. Y may be the same as defined in Formula 4.

In an implementation, in Formula 3 and Formula 4, Y may include a sulfonate group having 1 to 10 carbon atoms. In an implementation, in Formula 3 and Formula 4, Y may be represented by the following Formula Y.

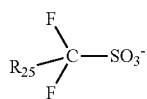

[Formula Y]

In Formula Y, $R_{25}$ may include, e.g., hydrogen, a halogen, or a substituted or unsubstituted alkyl group having 1 to 5 carbon atoms.

In an implementation, in Formula Y, $R_{25}$ may be, e.g., fluorine or iodine.

The resist composition may further include a quencher. The quencher may be a photo decomposable quencher (PDQ). The quencher may include a compound represented by the following Formula 5 or a material represented by the following Formula 6.

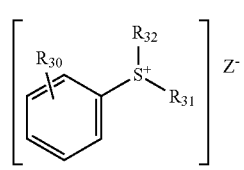

[Formula 5]

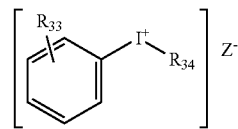

[Formula 6]

In Formula 5, $R_{30}$ may be or may include, e.g., hydrogen, a halogen, or a substituted or unsubstituted alkyl group having 1 to 5 carbon atoms. $R_{31}$ and $R_{32}$ may each independently be or include, e.g., an alkyl group having 1 to 7 carbon atoms or a substituted or unsubstituted aromatic ring group having 4 to 20 carbon atoms. Z may be a conjugate base of a weak acid.

In Formula 6, $R_{33}$ may be or may include, e.g., hydrogen, a halogen, or a substituted or unsubstituted alkyl group having 1 to 5 carbon atoms. $R_{34}$ may be or may include, e.g., an alkyl group having 1 to 7 carbon atoms or a substituted or unsubstituted aromatic ring group having 4 to 20 carbon atoms. Z may be a conjugate base of a weak acid.

In an implementation, the compound represented by Formula 5 may include a compound represented by Formula 5A. The compound represented by Formula 6 may include a compound represented by Formula 6A.

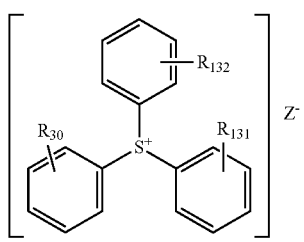

[Formula 5A]

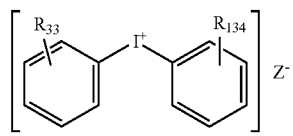

[Formula 6A]

In Formula 5A, $R_{30}$, $R_{131}$ and $R_{132}$ may each independently be or include, e.g., hydrogen, a halogen, or a substituted or unsubstituted alkyl group having 1 to 5 carbon atoms, and Z may be defined the same as in Formula 5.

In Formula 6A, $R_{33}$ and $R_{134}$ may each independently be or include, e.g., hydrogen, a halogen, or a substituted or unsubstituted alkyl group having 1 to 5 carbon atoms, and Z may be defined the same as in Formula 6.

In an implementation, in Formula 5 and Formula 6, Z may include a carboxylate group having 1 to 10 carbon atoms. In an implementation, in Formula 5 and Formula 6, Z may include a group represented by the following Formula Z.

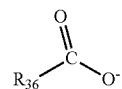

[Formula Z]

In Formula Z, $R_{36}$ may include, e.g., hydrogen, a halogen, or a substituted or unsubstituted alkyl group having 1 to 9 carbon atoms.

The resist composition may further include an organic solvent. The organic solvent may be a nonpolar solvent. In an implementation, the organic solvent may include, e.g., propylene glycol methyl ether acetate (1-methoxy-2-propyl acetate, PGMEA), propylene glycol methyl ether (1-methoxy-2-propanol, PGME), ethylene glycol (ethane-1, 2-diol, EL), gamma-butyrolactone (GBA), or diacetone alcohol (DAA). The compound represented by Formula 1 may have high solubility with respect to the organic solvent. A polymer, a photo-acid generator, a quencher, and the compound represented by Formula 1 may be dissolved in the organic solvent to prepare a resist composition.

Hereinafter, a compound represented by Formula 1 according to an embodiment and the exposure process of a resist composition including the compound will be explained in more detail.

In an implementation, the compound represented by Formula 1 may be represented by Formula 1A below. In an implementation, the compound represented by Formula 1A may include indene, fluorene, or a derivative thereof.

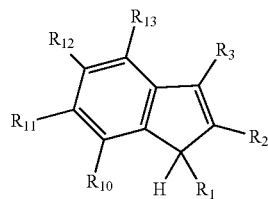

[Formula 1A]

In Formula 1A, $R_1$, $R_{10}$, $R_{11}$, $R_{12}$ and $R_{13}$ may each independently be or include, e.g., hydrogen, a halogen, a substituted or unsubstituted alkyl group having 1 to 7 carbon atoms, a substituted or unsubstituted carbonyl group having 1 to 7 carbon atoms, a substituted or unsubstituted ester group having 1 to 7 carbon atoms, a substituted or unsubstituted acetal group having 1 to 7 carbon atoms, a substituted or unsubstituted alkoxy group having 1 to 7 carbon atoms, a substituted or unsubstituted ether group having 1 to 7 carbon atoms, or —COO(CH$_2$)CF$_2$SO$_3^-$. R$_2$ and R$_3$ may each independently be or include, e.g., hydrogen, a halogen, a substituted or unsubstituted alkyl group having 1 to 7 carbon atoms, a substituted or unsubstituted ester group having 1 to 7 carbon atoms, a substituted or unsubstituted acetal group having 1 to 7 carbon atoms, a substituted or unsubstituted alkoxy group having 1 to 7 carbon atoms, or a substituted or unsubstituted ether group having 1 to 7 carbon atoms. In an implementation, R$_2$ and R$_3$ may be separate or may be combined with each other to form an aromatic ring having 3 to 20 carbon atoms.

In Formula 1 and Formula 1A, when R$_2$ and R$_3$ are combined with each other to form an aromatic ring having 3 to 20 carbon atoms, the aromatic ring may be substituted or unsubstituted. In Formula 1 and Formula 1A, when R$_2$ and R$_3$ are combined with each other to form an aromatic ring having 3 to 20 carbon atoms, R$_2$ and R$_3$ may be represented by, e.g., the following Formula A.

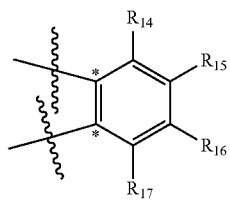

[Formula A]

In Formula A, R$_{14}$, R$_{15}$, R$_{16}$, and R$_{17}$ may each independently be or include, e.g., hydrogen, a halogen, an alkyl group having 1 to 7 carbon atoms, a carbonyl group having 1 to 7 carbon atoms, an ester group having 1 to 7 carbon atoms, an acetal group having 1 to 7 carbon atoms, an alkoxy group having 1 to 7 carbon atoms, or an ether group having 1 to 7 carbon atoms. In Formula A, each of the parts represented by * may mean carbon bonded to R$_2$ or R$_3$ in Formula 1 or Formula 1A.

In an implementation, the compound represented by Formula 1A may be represented by Formula 1B below. In an implementation, the compound represented by Formula 1B may include fluorene or a derivative thereof.

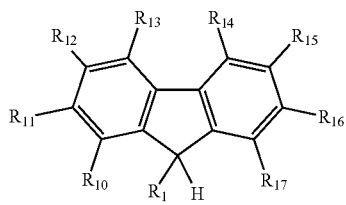

[Formula 1B]

In Formula 1B, R$_1$, R$_{10}$, R$_{11}$, R$_{12}$, R$_{13}$, R$_{14}$, R$_{15}$, R$_{16}$ and R$_{17}$ may each independently be or include, e.g., hydrogen, a halogen, a substituted or unsubstituted alkyl group having 1 to 7 carbon atoms, a substituted or unsubstituted carbonyl group having 1 to 7 carbon atoms, a substituted or unsubstituted ester group having 1 to 7 carbon atoms, a substituted or unsubstituted acetal group having 1 to 7 carbon atoms, a substituted or unsubstituted alkoxy group having 1 to 7 carbon atoms, a substituted or unsubstituted ether group having 1 to 7 carbon atoms, or —COO(CH$_2$)CF$_2$SO$_3^-$.

The compound represented by Formula 1A may play the role of a photosensitive agent. In an implementation, the compound represented by Formula 1A may have a high HOMO energy level. During performing the exposure process of a resist layer, a polymer may absorb the photons of light and emit electrons and hydrogen ions (H$^+$) to form a polymer having a modified structure. The light may be extreme ultraviolet radiation. In an implementation, the polymerization unit represented by Formula 2A of the polymer may absorb the photons of light and emit electrons and hydrogen ions. The emission reaction of electrons and hydrogen ions of a polymer according to an embodiment may be performed as in the following Reaction 1:

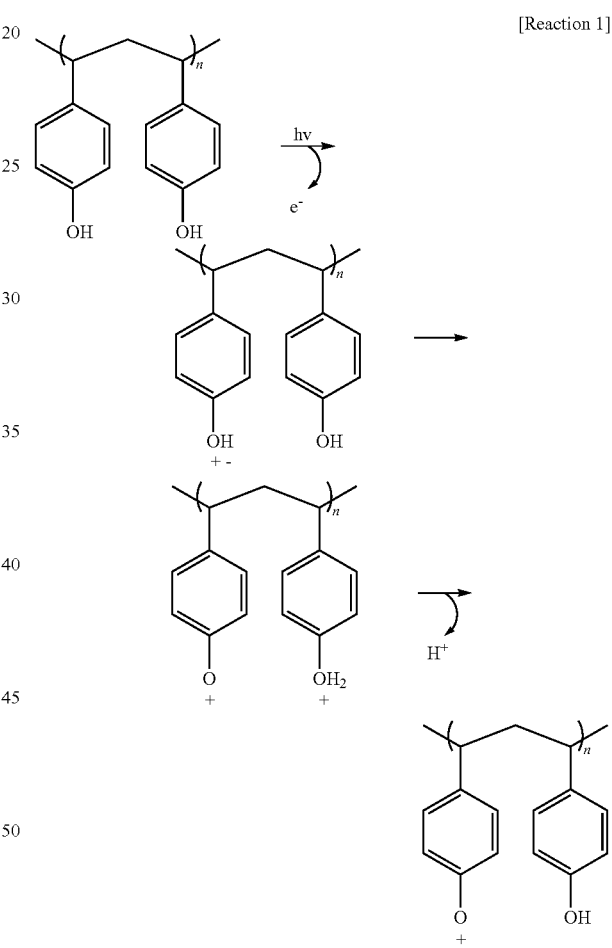

[Reaction 1]

The polymerization unit represented by Formula 2B of the polymer may react with electrons or hydrogen ions thus produced and may be decomposed. In an implementation, the ester group of the polymerization unit represented by Formula 2B may react with the hydrogen ions to form a carboxylic acid. The polymerization unit forming the carboxylic acid may be a polymer having a modified structure, and the exposed portion of the resist layer may include the polymer having a modified structure. The forming reaction of the carboxylic acid may be referred to as deprotection reaction.

The extreme ultraviolet radiation has high energy per photon, and smaller photon number may be included by the same amount of exposure when compared with the light of a KrF exposure process. If the photosensitive agent were to be omitted, due to small photon numbers, the deprotection reaction efficiency of the polymer may be reduced. The sufficient formation of a modified polymer in the exposed portion of the resist layer may become difficult. Due to photon shot noise effects, a resist pattern may have a relatively large line width roughness.

According to embodiments, the compound represented by Formula 1A may have a high HOMO energy level and low ionization potential. For example, the compound represented by Formula 1A may have a higher HOMO energy level than the polymerization unit represented by Formula 2A (e.g., polyhydroxystyrene). In an implementation, the material represented by Formula 1A may have a HOMO energy level higher than about −8.50 eV.

Hydrogen bonded to the carbon at the benzylic position of the compound represented by Formula 1A or the compound represented by Formula 1B may easily undergo deprotonation reaction to form a hydrogen ion and a carbocation at the benzylic position. In an implementation, the carbon at the benzylic position may be carbon to which $R_1$ is bonded in Formula 1A and Formula 1B. The compound represented by Formula 1A and the compound represented by Formula 1B may form secondary electrons and radical at the benzylic position by photons. The radical may be a carbon-centered radical. The carbocation and radical at the benzylic position may be stable due to the p orbital delocalization of an aromatic ring. Accordingly, the photosensitive agent may be easily activated by a small number of photons to produce secondary electrons and hydrogen ions. In an implementation, the deprotection reaction efficiency of a polymer may be improved. The hydrogen ion production reaction of the material represented by Formula 1A according to an embodiment may be performed by Reaction 2A below. The hydrogen ion production reaction of the compound represented by Formula 1B according to an embodiment may be performed as Reaction 2B below.

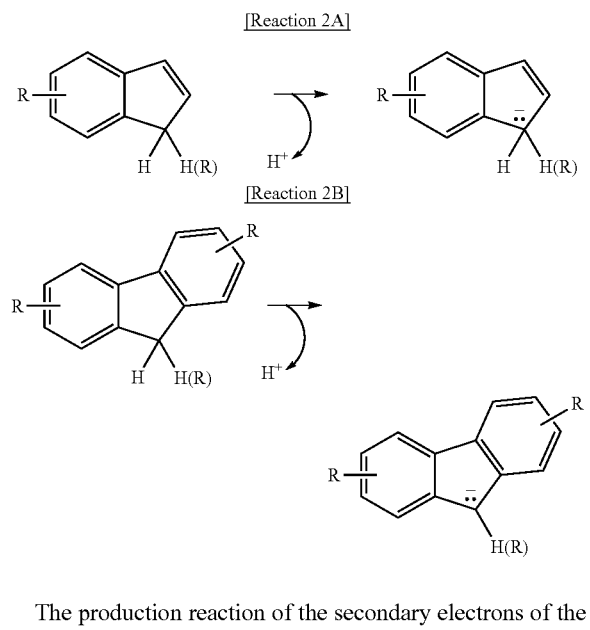

The production reaction of the secondary electrons of the compound represented by Formula 1A according to an embodiment may be performed by Reaction 3A below. The production reaction of the secondary electrons of the compound represented by Formula 1B according to an embodiment may be performed by Reaction 3B below.

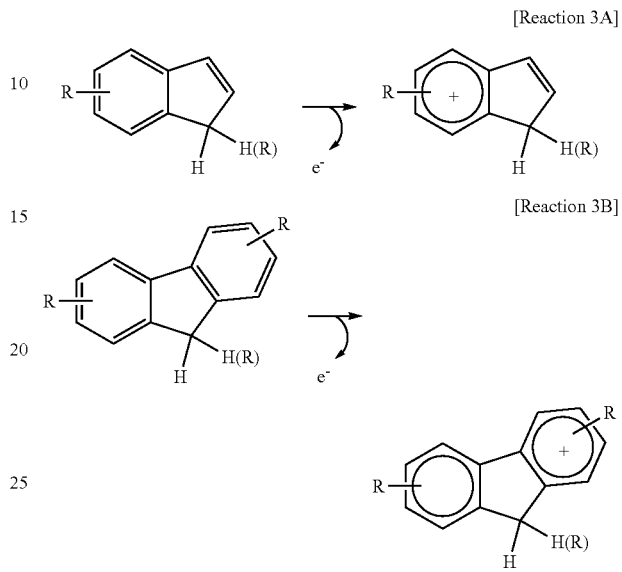

In Reaction 2A, Reaction 2B, Reaction 3A and Reaction 3B, R may be hydrogen, a halogen, an alkyl group having 1 to 7 carbon atoms, a carbonyl group having 1 to 7 carbon atoms, an ester group having 1 to 7 carbon atoms, an acetal group having 1 to 7 carbon atoms, an alkoxy group having 1 to 7 carbon atoms, or an ether group having 1 to 7 carbon atoms.

In an implementation, the resist composition may include a photosensitive agent, and the deprotection reaction efficiency of the polymer may increase, and the generation of photon shot effects may be prevented. Accordingly, the efficiency of an exposure process and accuracy may be improved. In an implementation, the resist pattern may be formed with high accuracy, and the line width uniformity may be improved.

During the exposure process, the photo-acid generator may produce hydrogen ions by the photons of light. The production of hydrogen ions from the photo-acid generator may be performed by Reaction 4 below. The hydrogen ions produced from the photo-acid generator may promote the formation of a modified polymer.

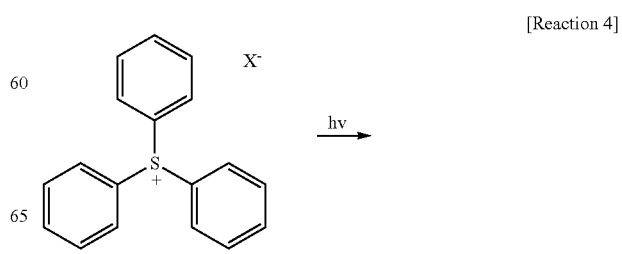

-continued

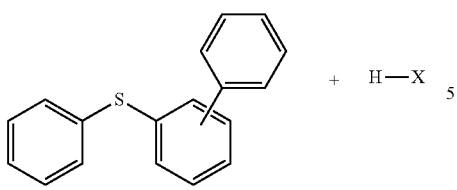
+ H—X

In Reaction 4, X may be the same as defined in Formula 3 above.

Hereinafter, an exemplary preparation method of a material represented by Formula 1 according to embodiments will be explained.

A material represented by Formula 1 may be prepared by the following Reaction A, Reaction B, Reaction C, Reaction D, or Reaction E:

[Reaction A]

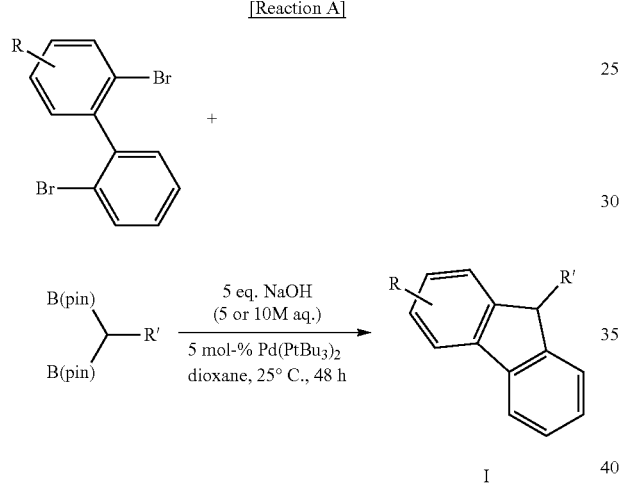

In Reaction A, R' and R are the same as $R_1$ and $R_{10}$, respectively, of Formula 1B.

In Reaction A, tBu is tertiary butyl, and B(pin) is (pinacolato)boron represented by $(CH_3)_4C_2O_2B$.

[Reaction B]

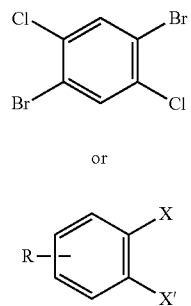

or +

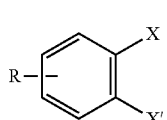

R = H, CH$_3$, OCH$_3$
X = Cl, Br
X' = Cl, Br, I

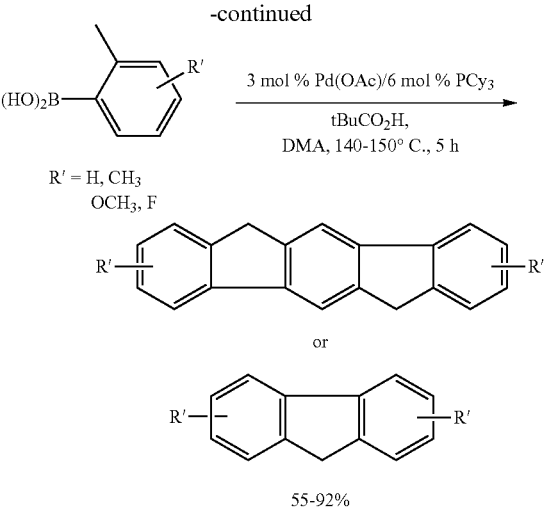

R' = H, CH$_3$
OCH$_3$, F 55-92%

In Reaction B, Ac is acetyl ($C_2H_3O$), tBu is tertiary butyl, PCy$_3$ is tricyclohexylphosphine (CAS Number 2622-14-2), and DMA is dimethyl amine.

[Reaction C]

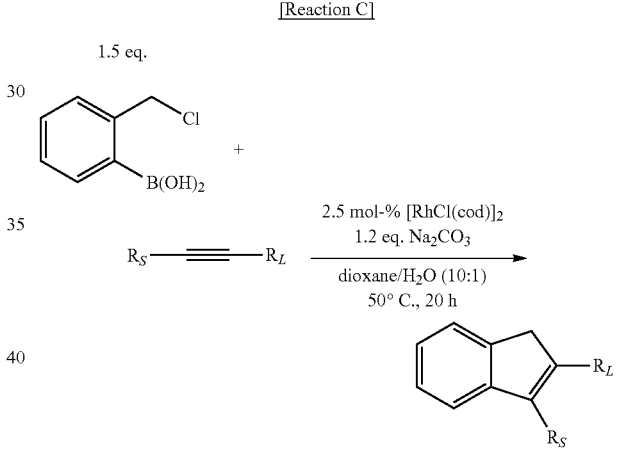

In Reaction C, [RhCl(cod)]$_2$ is chloro(1,5-cyclooctadiene)rhodium(I) dimer (CAS Number 12092-47-6), and R$_S$ and R$_L$ are the same as R$_2$ and R$_3$, respectively, of Formula 1A.

[Reaction D]

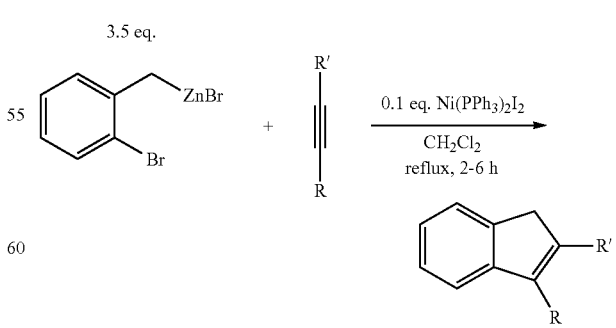

In Reaction D, Ni(PPh$_3$)$_2$I$_2$ is diiodobis(triphenylphosphine)nickel(II) (CAS Number 787624-20-8), and R' and R are the same as R$_2$ and R$_3$, respectively, of Formula 1A.

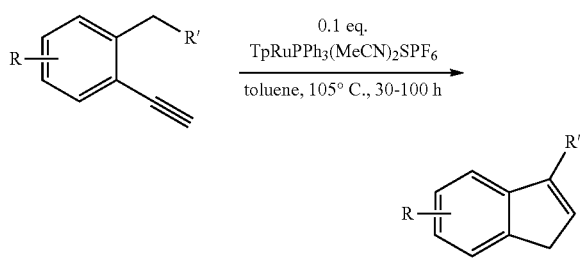

In Reaction E, Tp is tris(1-pyrazolyl)borate, Ph is phenyl, Me is $CH_3$, and R and R' are the same as $R_3$ and $R_{10}$, respectively, of Formula 1A.

Hereinafter, the resist composition and the formation of a resist pattern using thereof will be explained referring to Experimental Examples and a Comparative Example.

1. Comparative Example

A polymer, a photo-acid generator and a quencher were mixed to prepare a resist composition. The resist composition was applied on a substrate to form a resist layer. On the resist layer, an exposure process and a developing process were performed to form a resist pattern. In this case, the resist pattern had holes as shown in FIG. 1A, which will be explained below. The line width uniformity (hereinafter, will be referred to as "CD uniformity") of the resist pattern was measured.

2. Experimental Example 1

A resist composition and a resist pattern are prepared by the same method described in the Comparative Example, and the CD uniformity of the resist pattern was measured. However, a polymer, a photo-acid generator, a quencher, and fluorene were mixed to prepare a resist composition. The amount of the fluorene was 20% of the weight of the polymer.

3. Experimental Example 2

A resist composition and a resist pattern are prepared by the same method described in the Comparative Example and the CD uniformity of the resist pattern was measured. However, a polymer, a photo-acid generator, a quencher, and fluorene were mixed to prepare a resist composition. The amount of the fluorene was 50% of the weight of the polymer.

Table 1 shows the CD uniformity and the improvement of the CD uniformity of each of the Comparative Example, Experimental Example 1, and Experimental Example 2. The amounts of the photosensitive agent correspond to results obtained by calculating (weight of photosensitive agent/weight of polymer)×100, and the improvement corresponds to results obtained by calculating a CD uniformity difference by percent of each of the Experimental Examples and the Comparative Example with respect to the CD uniformity of the Comparative Example.

TABLE 1

|  | Amount of photosensitive agent (fluorene) | CD uniformity (nm) | Improvement (%) |
| --- | --- | --- | --- |
| Comparative Example | — | 3.28 | — |
| Experimental Example 1 | 20% | 3.20 | 2.5% |
| Experimental Example 2 | 50% | 3.14 | 4.3% |

Referring to Table 1, the CD uniformity of Experimental Example 1 and Experimental Example 2 were smaller than that of Comparative Example. Experimental Example 1 and Experimental Example 2 may have improved CD uniformity than Comparative Example. According to embodiments, the resist composition includes a photosensitive agent, and the resist pattern having a uniform line width may be formed.

In an implementation, in Formula 1, $R_1$ may be represented by Formula R above. In an implementation, the compound represented by Formula 1 may represented by the following Formula A-1.

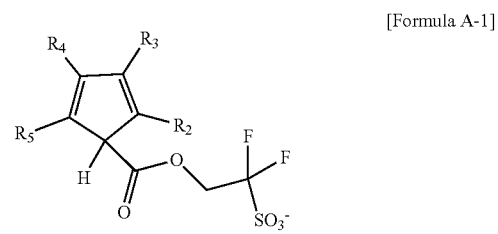

[Formula A-1]

In Formula A-1, $R_2$, $R_3$, $R_4$ and $R_5$ may be defined the same as those of Formula 1 above. In an implementation, $R_2$, $R_3$, $R_4$ and $R_5$ may each independently be or include, e.g., hydrogen, a halogen, a substituted or unsubstituted alkyl group having 1 to 7 carbon atoms, a substituted or unsubstituted carbonyl group having 1 to 7 carbon atoms, a substituted or unsubstituted ester group having 1 to 7 carbon atoms, an acetal group having 1 to 7 carbon atoms, an alkoxy group having 1 to 7 carbon atoms, or an ether group having 1 to 7 carbon atoms. In an implementation, $R_2$, $R_3$, $R_4$ and $R_5$ may be separate, or adjacent ones thereof may be combined to form an aromatic ring having 3 to 20 carbon atoms.

In an implementation, in Formula A-1, $R_2$ and $R_3$ may be combined with each other to form an aromatic ring represented by Formula A. In Formula A, each of the parts represented by * may mean carbon bonded to $R_4$ or $R_5$ in Formula A-1.

In an implementation, in Formula A-1, when $R_2$ and $R_3$ are combined with each other to form an aromatic ring having 3 to 20 carbon atoms, the aromatic ring may be substituted or unsubstituted. In Formula A-1, $R_4$ and $R_5$ may be combined with each other to form an aromatic ring represented by the following Formula B.

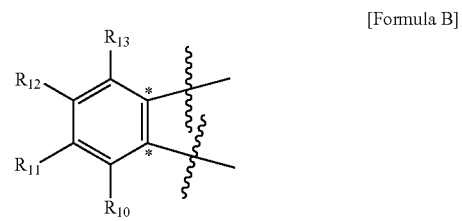

[Formula B]

In Formula B, $R_{10}$, $R_{11}$, $R_{12}$ and $R_{13}$ may each independently be or include, e.g., hydrogen, a halogen, an alkyl group having 1 to 7 carbon atoms, a carbonyl group having 1 to 7 carbon atoms, an ester group having 1 to 7 carbon atoms, an acetal group having 1 to 7 carbon atoms, an alkoxy group having 1 to 7 carbon atoms, or an ether group having 1 to 7 carbon atoms. In Formula B, each of the parts represented by * may mean carbon bonded to $R_4$ or $R_5$ in Formula A-1.

In an implementation, the material represented by Formula A-1 may include the materials represented by the following Formula 1-1 to Formula 1-6:

[Formula 1-1]
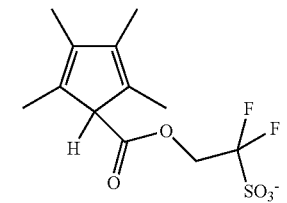

[Formula 1-2]
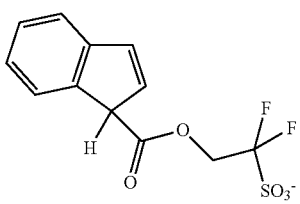

[Formula 1-3]
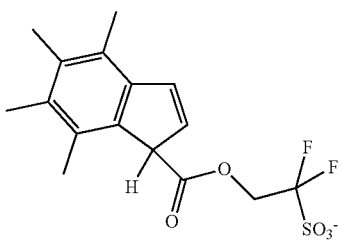

[Formula 1-4]
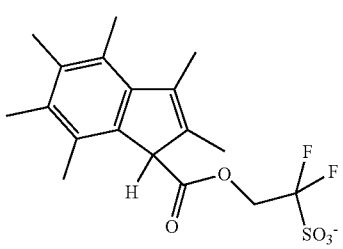

[Formula 1-5]
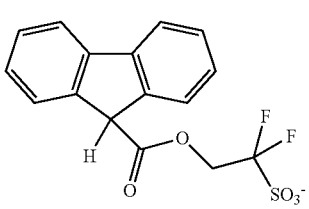

[Formula 1-6]
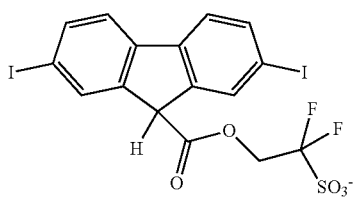

According to embodiments, the compound represented by Formula A-1 may be a photo-acid generator. The photo-acid generator may produce hydrogen ions ($H^+$) during the exposure process of a resist layer. In an implementation, the compound represented by Formula A-1 may perform deprotonation reaction to produce hydrogen ions and carbocation of a benzylic position. The carbon of the benzylic position may be a carbon bonded to $—COO(CH_2)CF_2SO_3^-$. The carbocation of the benzylic position may be very stable due to p orbital delocalization and a resonance structure. At the benzylic position, a functional group substituted with sulfonate and fluorine (e.g., $—COO(CH_2)CF_2SO_3^-$) may be bonded, and the carbocation of the benzylic position may be more stable. In the exposure process using extreme ultraviolet radiation, the compound represented by Formula A-1 may be easily activated by a small number of photons and may easily produce hydrogen ions. Accordingly, the efficiency of the deprotection reaction of a polymer and the efficiency of the exposure process may be improved.

The compound represented by Formula A-1 may be an anion. In an implementation, the photo-acid generator may further include a cation, and the cation may be represented by Formula A-2 or Formula A-3 below. An equivalent ratio or number of equivalents of the compound represented by Formula A-1 may be the same as a sum of equivalents of the compounds represented by Formula A-2 and Formula A-3 (e.g., such that the ions are balanced to form a charge neutral compound).

[Formula A-2]
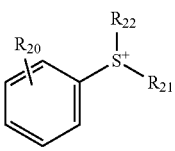

[Formula A-3]
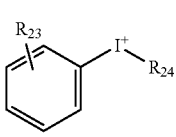

In Formula A-2, $R_{20}$ may be or may include, e.g., hydrogen, a halogen, or a substituted or unsubstituted alkyl group having 1 to 5 carbon atoms. $R_{21}$ and $R_{22}$ may each independently be or include, e.g., an alkyl group having 1 to 7 carbon atoms, or a substituted or unsubstituted aromatic ring compound having 4 to 20 carbon atoms.

In Formula A-3, $R_{23}$ may be or may include, e.g., hydrogen or a substituted or unsubstituted alkyl group having 1 to 5 carbon atoms. $R_{24}$ may be or may include, e.g., an alkyl group having 1 to 7 carbon atoms or a substituted or unsubstituted aromatic ring compound having 4 to 20 carbon atoms.

In an implementation, the compound represented by Formula A-2 may be represented by the following Formula AA-2.

[Formula AA-2]
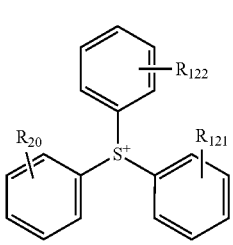

In Formula AA-2, $R_{20}$, $R_{121}$ and $R_{122}$ may each independently be or include, e.g., hydrogen, a halogen, or a substituted or unsubstituted alkyl group having 1 to 5 carbon atoms.

In an implementation, the compound represented by Formula A-3 may be represented by the following Formula AA-3.

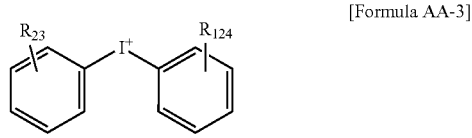

[Formula AA-3]

In Formula AA-3, $R_{23}$, and $R_{124}$ may each independently be or include, e.g., hydrogen, a halogen, or a substituted or unsubstituted alkyl group having 1 to 5 carbon atoms.

If the resist composition were to not include the compound represented by Formula 1, and an aromatic ring compound having hydrogen at a benzylic position were combined with or part of the polymerization unit of a polymer, the efficiency of forming a resist pattern may be reduced. For example, during an exposure process, electrons and hydrogen ions emitted from the polymer may decrease, or the formation of a polymer having a modified structure may decrease. According to embodiments, the resist composition may separately include a polymer and the compound represented by Formula 1, e.g., the compound represented by Formula 1 may not form any chemical bond with the polymer. In an implementation, the material represented by Formula 1 may be provided in the resist composition in a monomolecular state. Accordingly, the resist layer using the resist composition may have high sensitivity with respect to light. The efficiency of forming the resist pattern may be improved.

In an implementation, the resist composition may include the compound represented by Formula 1A and the compound represented by Formula A-1. In this case, the compound represented by Formula 1A may play the role of a photosensitive agent, and the compound represented by Formula A-1 may play the role of a photo-acid generator.

In an implementation, the resist composition may include a polymer, a photo-acid generator, and the compound represented by Formula 1A. The anion of the photo-acid generator may be different from the compound represented by Formula A-1. In an implementation, the photo-acid generator may include the compound represented by Formula 3 and the compound represented by Formula 4.

In an implementation, the resist composition may include a polymer and the compound represented by Formula A-1, and may not include the compound represented by Formula 1A.

In an implementation, in Formula 1, Formula 1A, Formula 1B, and Formula A-1, the ester group may be —OOC—$R_{40}$ or —COO—$R_{40}$, the acetal group may be —$CR_{41}(OR_{42})(OR_{43})$, the ether group may be —$OR_{44}$, the carbonyl group may be —$COR_{45}$, $R_{40}$, $R_{41}$, $R_{42}$, $R_{43}$ and $R_{45}$ may be each independently an alkyl group having 1 to 6 carbon atoms, and $R_{44}$ may be an alkyl group having 1 to 7 carbon atoms. A total number of carbon atoms of $R_{41}$, $R_{42}$ and $R_{43}$ may be 7 or less.

According to an embodiment, the compound represented by Formula 1 may include a halogen. In an implementation, at least one among $R_1$, $R_2$, $R_3$, $R_4$ and $R_5$ of Formula 1, at least one among $R_1$, $R_2$, $R_3$, $R_{10}$, $R_{11}$, $R_{12}$ and $R_{13}$ of Formula 1A, at least one among $R_1$, $R_{10}$, $R_{11}$, $R_{12}$, $R_{13}$, $R_{14}$, $R_{15}$, $R_{16}$ and $R_{17}$ of Formula 1B, or at least one among $R_2$, $R_3$, $R_4$ and $R_5$ of Formula A-1 may include a halogen. In an implementation, the halogen may include fluorine or iodine.

The fluorine and iodine may have excellent extreme ultraviolet absorption properties. If the compound represented by Formula 1 includes fluorine or iodine, improved absorption properties of the photons of extreme ultraviolet radiation may be achieved, and high emission efficiency on secondary electrons or hydrogen ions may be achieved.

Hereinafter, a method of forming a pattern and a method of manufacturing a semiconductor device using the resist composition according to embodiments will be explained.

Figure 1B:
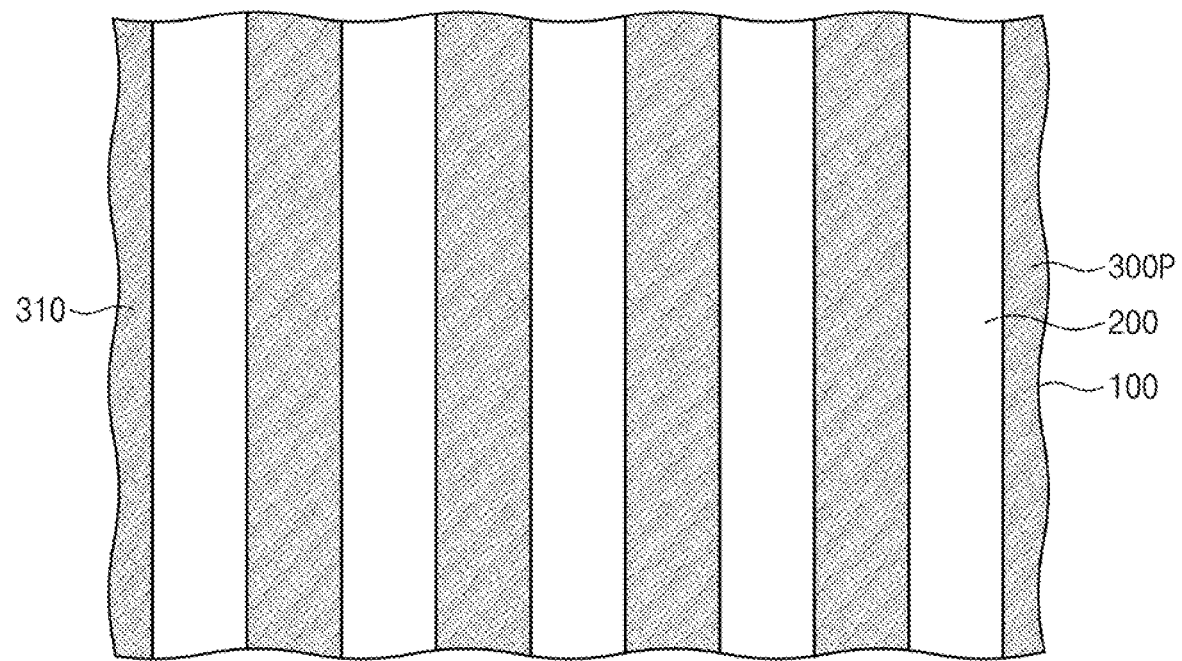
FIG. 1B is a plan view showing a resist pattern according to embodiments.

FIG. 1A is a plan view showing a resist pattern according to embodiments. FIG. 1B is a plan view showing a resist pattern according to embodiments. FIG. 2 to FIG. 6 are diagrams of stages in a method of forming a pattern according to embodiments, which correspond to cross-sections taken along line I-II in FIG. 1A.

Figure 2:
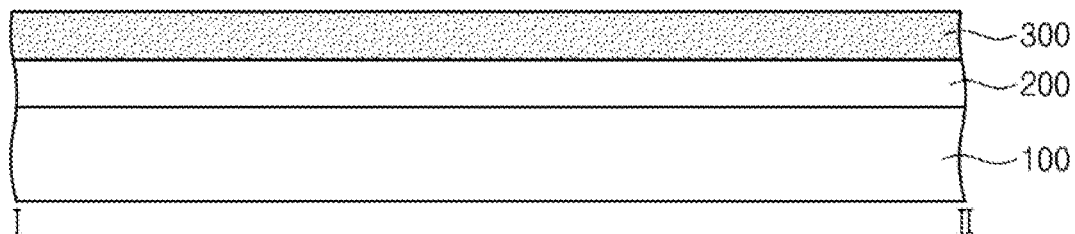
FIG. 2 to FIG. 6 are diagrams of stages in a method of forming a pattern according to embodiments.

Referring to FIG. 1A and FIG. 2, a substrate 100 may be prepared. A lower layer 200 and a resist layer 300 may be formed on the substrate 100 in order. The lower layer 200 may be a target layer to be etched. The lower layer 200 may be formed using a semiconductor material, a conductive material, an insulating material, or combinations thereof. The lower layer 200 may be formed as a single layer or a plurality of stacked layers. In an implementation, layers may be further provided between the substrate 100 and the lower layer 200.

The resist composition according to embodiments may be applied on the lower layer 200 to form the resist layer 300. The application of the resist composition may be performed by spin coating. On the resist compound thus applied, a heating process may be further performed. The heating process may correspond to the baking process of the resist layer 300.

Figure 3:
Figure 3:
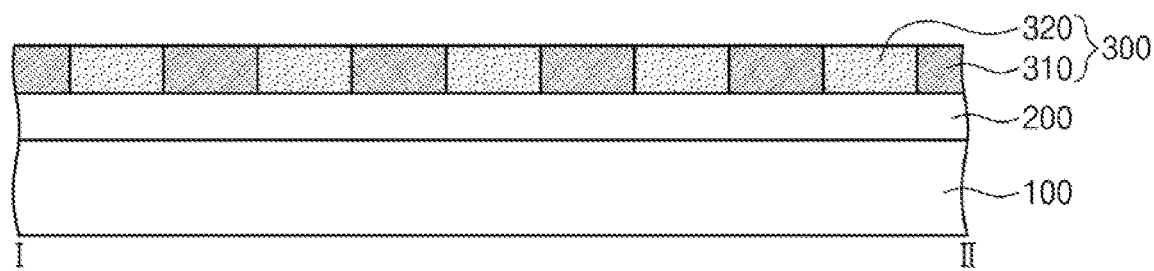

Referring to FIG. 1A and FIG. 3, the resist layer 300 may be exposed to light (e.g., electromagnetic radiation or other energy) 500. The light 500 may be an electron beam or extreme ultraviolet radiation. Before irradiating the light 500, a photo mask 400 may be disposed on the resist layer 300. The light 500 may be irradiated onto the first part 310 of the resist layer 300, exposed by the photo mask 400.

When the resist layer 300 is exposed to the light 500, the polymer may undergo deprotection reaction by electrons and hydrogen ions as explained above, and a polymer having a modified structure may be formed. The material represented by Formula 1 may produce secondary electrons and hydrogen ions. The resist composition may include the compound represented by Formula 1, the efficiency of the deprotection reaction of the polymer may be improved, and the polymer having a modified structure may be formed in higher efficiency. The first part 310 of the resist layer 300 may be rapidly formed, and the first part 310 of the resist layer 300 may be formed in a desired position with high accuracy.

The second part 320 of the resist layer 300 may be unexposed to the light 500. The chemical structure of the resist compound in the second part 320 of the resist layer 300 may be unchanged. After finishing the irradiation of the light 500, the material of the first part 310 of the resist layer 300 may have a different chemical structure from the material of the second part 320. If electrons or hydrogen ions produced in the first part 310 of the resist layer 300 were to move to the second part 320, the second part 320 may include a polymer having a modified structure. A quencher may help prevent the movement of the electrons or hydrogen ions produced in the first part 310 to the second part 320. The light 500 may include extreme ultraviolet radiation, and the first part 310 and the second part 320 of the resist layer 300 may be formed to have a narrow width. Then, the photo mask 400 may be removed.

Figure 4:
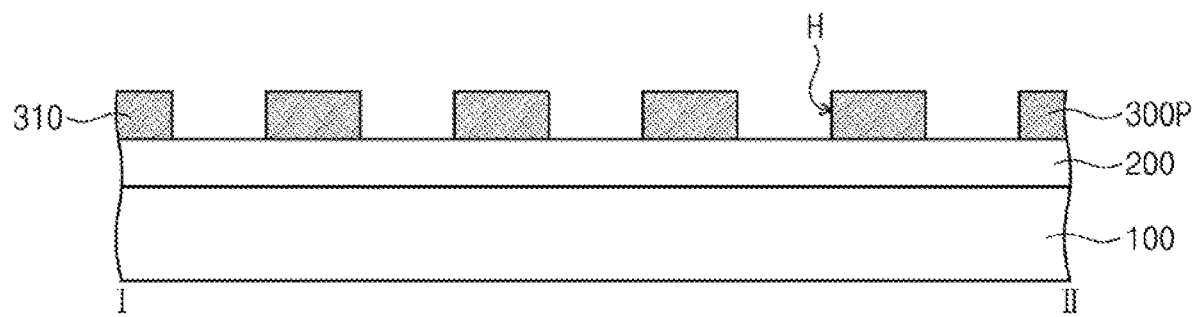

Referring to FIG. 1A and FIG. 4, the second part 320 of the resist layer 300 may be removed to form a resist pattern 300P. The second part 320 of the resist layer 300 may have reactivity to or solubility in a developing solution, and the first part 310 of the resist layer 300 may not have reactivity to or solubility in the developing solution. Accordingly, the second part 320 of the resist layer 300 may be selectively developed. The resist pattern 300P may correspond to the first part 310 of the resist layer 300. The resist pattern 300P may be formed by a patterning process including the exposing and developing processes of the resist layer 300. The resist pattern 300P may have improved CD uniformity. The extreme ultraviolet radiation has high energy per one photon, and the resist pattern 300P may be formed to have a minute width (W) and pitch.

The resist pattern 300P may expose the lower layer 200. In an implementation, the resist pattern 300P may have a plurality of holes H, and the holes H may expose the lower layer 200.

In an implementation, as illustrated in FIG. 1A, the plurality of holes H of the resist pattern 300P may have a circular shape. The holes H of the resist pattern 300P may be arranged in a honeycomb shape. The planar shape of the resist pattern 300P and the holes H may be changed into various shapes.

Referring to FIG. 1B, the resist pattern 300P may have a linear planar shape. In an implementation, the resist pattern 300P may include parts extended (e.g., lengthwise) in one direction.

In an implementation, the planar shape of the resist pattern 300P may be changed into various shapes such as a zigzag shape, a polygonal shape and a circular shape.

Figure 5:
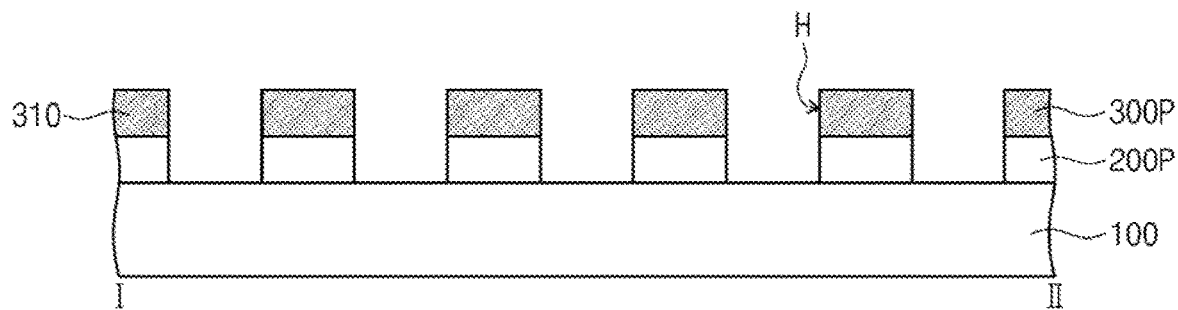

Referring to FIG. 1A and FIG. 5, the lower layer 200 exposed by the resist pattern 300P may be removed to form a lower pattern 200P. The removal of the lower layer 200 may be performed by an etching process. During the etching process, the lower layer 200 may have etching selectivity with respect to the resist pattern 300P. The lower pattern 200P may expose the substrate 100. In an implementation, the lower pattern 200P may expose another layer between the substrate 100 and the lower pattern 200P. The resist pattern 300P may have improved CD uniformity, and the uniformity of the width of the lower pattern 200P may be improved. The resist pattern 300P may be formed at a desired position with high accuracy, and the patterning accuracy of the lower pattern 200P may be improved. The width of the lower pattern 200P may correspond to the width of the resist pattern 300P. The resist pattern 300P may have a narrow width, and the lower pattern 200P may be formed to have a narrow width.

Figure 6:
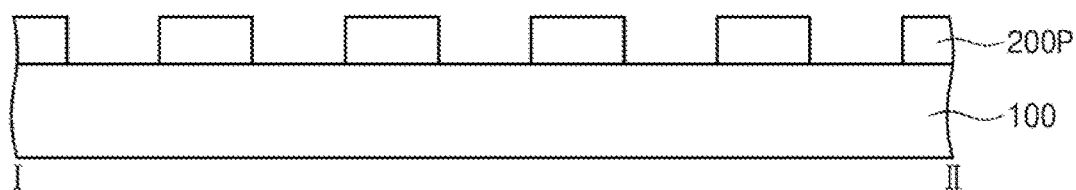

Referring to FIG. 1A and FIG. 6, the resist pattern 300P may be removed. Accordingly, the formation of a pattern may be completed. The pattern may mean the lower pattern 200P. By the preparation method explained hitherto, the patterning of the lower layer 200 and the formation of the lower pattern 200P may be completed.

According to embodiments, the lower pattern 200P may be an element of a semiconductor device. In an implementation, the lower pattern 200P may be a semiconductor pattern, a conductive pattern, or an insulating pattern in the semiconductor device.

Figure 7:
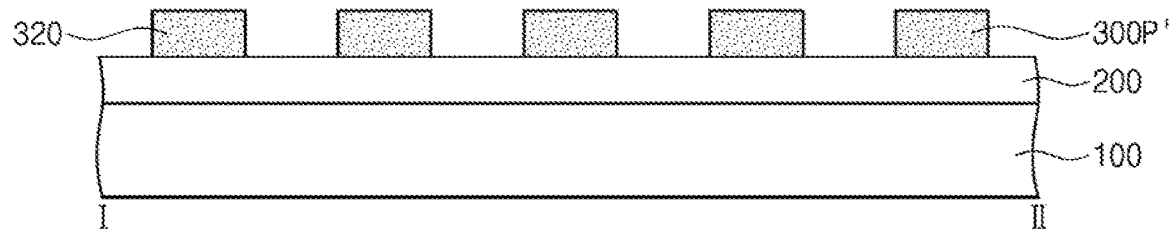
FIG. 7 and FIG. 8 are diagrams of stages in a method of forming a pattern according to other embodiments.
Figure 8:
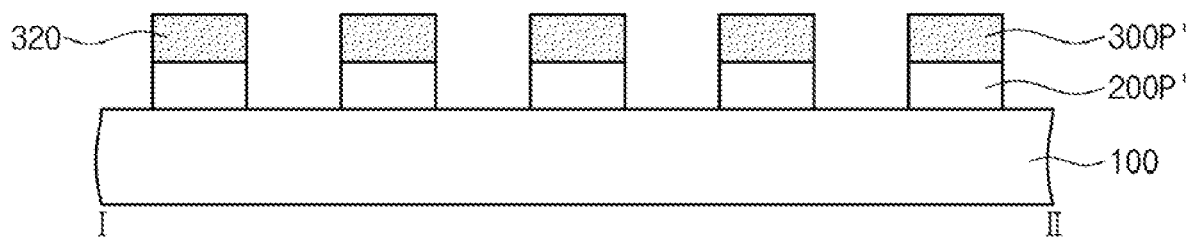

FIG. 7 and FIG. 8 are diagrams of stages in a method of manufacturing a semiconductor device according to other embodiments.

Referring to FIG. 2, a resist layer 300 and a lower layer 200 may be formed on a substrate 100.

Referring to FIG. 3, the first part 310 of the resist layer 300 may be exposed to light 500. After finishing the irradiation of the light 500, the material of the first part 310 of the resist layer 300 may have a different chemical structure from that of the material of the second part 320.

Referring to FIG. 7, the first part 310 of the resist layer 300 may be removed by a developing solution to form a resist pattern 300P'. The second part 320 of the resist layer 300 may not be removed by the developing solution. The resist pattern 300P' may correspond to the second part 320 of the resist layer 300.

Referring to FIG. 8, the lower layer 200 may be etched to from a lower pattern 200P'. The lower pattern 200P' may be formed at a position corresponding to the second part 320 of the resist pattern 300P'. The etching of the lower layer 200 may be performed by substantially the same method as the method explained referring to FIG. 5. Then, the resist pattern 300P' may be removed.

According to an embodiment, a composition may include an aromatic ring compound having hydrogen at a benzylic position, and a resist pattern may be formed using the composition. Accordingly, the efficiency of the preparation process of the resist pattern may be improved. The degrees of precision and accuracy of the resist pattern may be improved.

One or more embodiments may provide a photoresist composition.

One or more embodiments may provide a resist composition that exhibits improved reaction efficiency of an exposure process.

One or more embodiments may provide a method of forming a pattern having improved line width uniformity.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:
1. A resist composition, comprising:
a polymer; and
a compound represented by Formula 1,

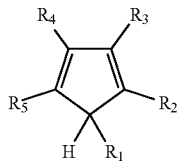

[Formula 1]

wherein, in Formula 1,
$R_1$ is a group represented by Formula R, and
$R_2$, $R_3$, $R_4$ and $R_5$ are each independently hydrogen, a halogen, a substituted or unsubstituted alkyl group having 1 to 7 carbon atoms, a substituted or unsubstituted ester group having 1 to 7 carbon atoms, a substituted or unsubstituted acetal group having 1 to 7 carbon atoms, a substituted or unsubstituted alkoxy group having 1 to 7 carbon atoms, or a substituted or unsubstituted ether group having 1 to 7 carbon atoms, $R_2$, $R_3$, $R_4$ and $R_5$ being separate or adjacent ones thereof are combined to form an aromatic ring having 3 to 20 carbon atoms,

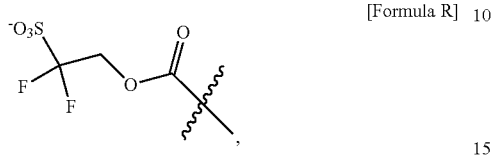

[Formula R]

provided that the compound represented by Formula 1 is not the following compound:

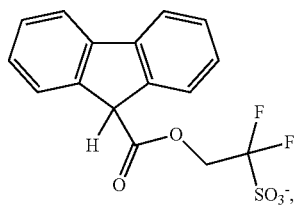

and
provided that when $R_2$ and $R_3$ are combined with each other to form an aromatic ring having 6 carbon atoms and $R_4$ and $R_5$ are combined with each other to form an aromatic ring having 6 carbon atoms, each aromatic ring having 6 carbon atoms is substituted with at least one of an ester group having 1 to 7 carbon atoms or an acetal group having 1 to 7 carbon atoms.

2. The resist composition as claimed in claim 1, wherein, in Formula 1, $R_2$ and $R_3$ are combined with each other to form an aromatic ring having 3 to 20 carbon atoms.

3. The resist composition as claimed in claim 2, wherein, in Formula 1, $R_4$ and $R_5$ are combined with each other to form an aromatic ring having 3 to 20 carbon atoms.

4. The resist composition as claimed in claim 1, wherein: the compound represented by Formula 1 is represented by Formula 1A,

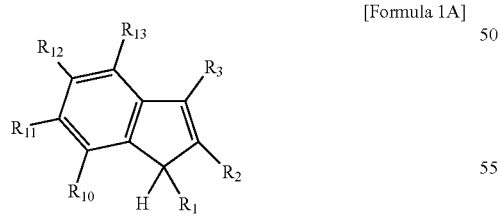

[Formula 1A]

in Formula 1A,
$R_1$ is defined the same as that of Formula 1,
$R_{10}$, $R_{11}$, $R_{12}$ and $R_{13}$ are each independently hydrogen, a halogen, an alkyl group having to 7 carbon atoms, a carbonyl group having 1 to 7 carbon atoms, an ester group having 1 to 7 carbon atoms, an acetal group having 1 to 7 carbon atoms, an alkoxy group having 1 to 7 carbon atoms, or an ester group having 1 to 7 carbon atoms, and $R_2$ and $R_3$ are each independently hydrogen, a halogen, an alkyl group having 1 to 7 carbon atoms, an ester group having 1 to 7 carbon atoms, an acetal group having 1 to 7 carbon atoms, an alkoxy group having 1 to 7 carbon atoms, or an ether group having 1 to 7 carbon atoms, $R_2$ and $R_3$ being separate or combined to form an aromatic ring having 3 to 20 carbon atoms.

5. The resist composition as claimed in claim 1, wherein: the compound represented by Formula 1 is represented by Formula 1B,

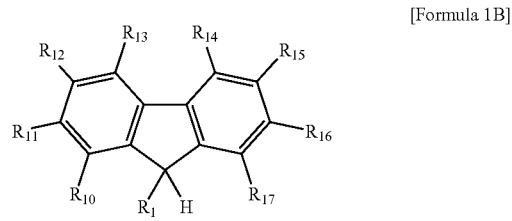

[Formula 1B]

in Formula 1B, $R_1$ is defined the same as that of Formula 1, and
$R_{10}$, $R_{11}$, $R_{12}$, $R_{13}$, $R_{14}$, $R_{15}$, $R_{16}$ and $R_{17}$ are each independently an ester group having 1 to 7 carbon atoms, or an acetal group having 1 to 7 carbon atoms.

6. The resist composition as claimed in claim 1, wherein: the compound represented by Formula 1 is represented by Formula A-1,

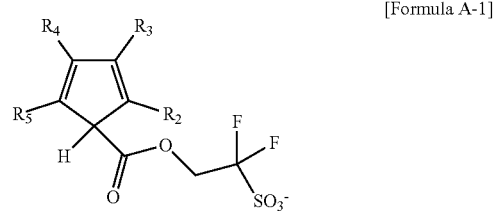

[Formula A-1]

in Formula A-1, $R_2$, $R_3$, $R_4$ and $R_5$ are each independently hydrogen, a halogen, an alkyl group having 1 to 7 carbon atoms, a carbonyl group having 1 to 7 carbon atoms, an ester group having 1 to 7 carbon atoms, an acetal group having 1 to 7 carbon atoms, an alkoxy group having 1 to 7 carbon atoms, or an ether group having 1 to 7 carbon atoms, $R_2$, $R_3$, $R_4$ and $R_5$ being separate or adjacent ones thereof are combined to form an aromatic ring having 3 to 20 carbon atoms.

7. The resist composition as claimed in claim 6, wherein: in Formula A-1, $R_4$ and $R_5$ are combined with each other such that Formula A-1 includes an aromatic ring represented by Formula B,

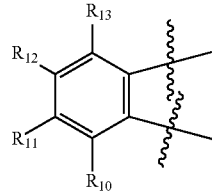

[Formula B]

in Formula B, $R_{10}$, $R_{11}$, $R_{12}$ and $R_{13}$ are each independently hydrogen, a halogen, an alkyl group having 1 to 7 carbon atoms, a carbonyl group having 1 to 7 carbon atoms, an ester group having 1 to 7 carbon atoms, an acetal group having 1 to 7 carbon atoms, an alkoxy group having 1 to 7 carbon atoms, or an ether group having 1 to 7 carbon atoms.

8. The resist composition as claimed in claim 7, wherein:
in Formula A-1, $R_2$ and $R_3$ are combined with each other such that Formula A-1 includes an aromatic ring represented by Formula A,

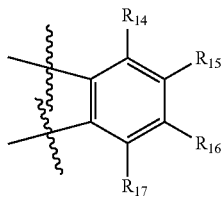

[Formula A]

in Formula A, $R_{14}$, $R_{15}$, $R_{16}$ and $R_{17}$ are each independently an ester group having 1 to 7 carbon atoms, or an acetal group having 1 to 7 carbon atoms.

9. The resist composition as claimed in claim 6, further comprising a compound represented by Formula A-2 or a compound represented by Formula A-3,
wherein:
a number of equivalents of the compound represented by Formula A-1 is the same as a sum of equivalents of the compound represented by Formula A-2 and the compound represented by Formula A-3 such that ions are balanced to form a charge neutral compound,

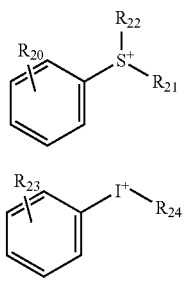

[Formula A-2]

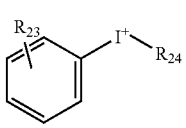

[Formula A-3]

in Formula A-2,
$R_{20}$ is hydrogen, a halogen, or a substituted or unsubstituted alkyl group having 1 to 5 carbon atoms, and
$R_{21}$ and $R_{22}$ are each independently an alkyl group having 1 to 7 carbon atoms or a substituted or unsubstituted aromatic ring group having 4 to 20 carbon atoms,
in Formula A-3,
$R_{23}$ is hydrogen, or a substituted or unsubstituted alkyl group having 1 to 5 carbon atoms, and
$R_{24}$ is an alkyl group having 1 to 7 carbon atoms or a substituted or unsubstituted aromatic ring group having 4 to 20 carbon atoms.

10. The resist composition as claimed in claim 1, further comprising a photo-acid generator and a quencher.

11. The resist composition as claimed in claim 1, wherein:
the polymer includes a polymerization unit represented by Formula 2A and a polymerization unit represented by Formula 2B,

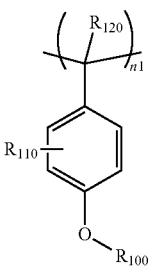

[Formula 2A]

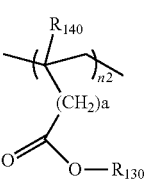

[Formula 2B]

in Formula 2A,
$R_{100}$, $R_{110}$ and $R_{120}$ are each independently hydrogen or a substituted or unsubstituted alkyl group having 1 to 7 carbon atoms, and
n1 is an integer of 1 to 1,000,000,
in Formula 2B,
$R_{130}$ is a substituted or unsubstituted tertiary alkyl group having 4 to 20 carbon atoms,
$R_{140}$ is hydrogen or a substituted or unsubstituted alkyl group having 1 to 7 carbon atoms,
a is an integer of 0 to 5,
n2 is an integer of 1 to 1,000,000,
n1+n2 is an integer of 50 to 1,000,001.

12. A composition, comprising:
a polymer;
a quencher;
a photo-acid generator represented by Formula A-1; and
a compound represented by Formula 1A,

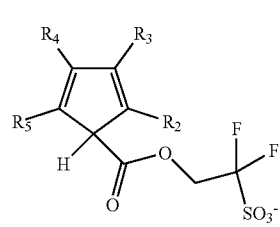

[Formula A-1]

wherein, in Formula A-1, $R_2$, $R_3$, $R_4$ and $R_5$ are each independently hydrogen, a halogen, an alkyl group having 1 to 7 carbon atoms, a carbonyl group having 1 to 7 carbon atoms, an ester group having 1 to 7 carbon atoms, an acetal group having 1 to 7 carbon atoms, an alkoxy group having 1 to 7 carbon atoms, or an ether group having 1 to 7 carbon atoms, $R_2$, $R_3$, $R_4$ and $R_5$ being separate or adjacent ones thereof are combined to form an aromatic ring having 3 to 20 carbon atoms, provided that the photo-acid generator represented by Formula A-1 is not the following compound:

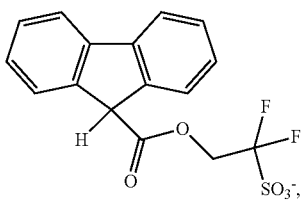

and
provided that when $R_2$ and $R_3$ of Formula A-1 are combined with each other to form an aromatic ring having 6 carbon atoms and $R_4$ and $R_5$ of Formula A-1 are combined with each other to form an aromatic ring having 6 carbon atoms, each aromatic ring having 6 carbon atoms is substituted with at least one of an ester group having 1 to 7 carbon atoms or an acetal group having 1 to 7 carbon atoms,

[Formula 1A]

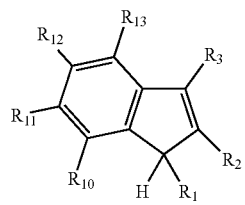

wherein, in Formula 1A,
$R_1$, $R_{10}$, $R_{11}$, $R_{12}$ and $R_{13}$ are each independently hydrogen, a halogen, a substituted or unsubstituted alkyl group having 1 to 7 carbon atoms, a substituted or unsubstituted carbonyl group having 1 to 7 carbon atoms, a substituted or unsubstituted ester group having 1 to 7 carbon atoms, a substituted or unsubstituted acetal group having 1 to 7 carbon atoms, a substituted or unsubstituted alkoxy group having 1 to 7 carbon atoms, a substituted or unsubstituted ether group having 1 to 7 carbon atoms, or —COO(CH$_2$)CF$_2$SO$_3^-$, and $R_2$ and $R_3$ are each independently hydrogen, a halogen, a substituted or unsubstituted alkyl group having 1 to 7 carbon atoms, a substituted or unsubstituted ester group having 1 to 7 carbon atoms, a substituted or unsubstituted acetal group having 1 to 7 carbon atoms, a substituted or unsubstituted alkoxy group having 1 to 7 carbon atoms, or a substituted or unsubstituted ether group having 1 to 7 carbon atoms, $R_2$ and $R_3$ being separate or combined with each other to form an aromatic ring having 3 to 20 carbon atoms.

13. The composition as claimed in claim 12, wherein, in Formula 1A, $R_2$ and $R_3$ are combined with each other to form a substituted or unsubstituted aromatic ring having to 20 carbon atoms.

14. The composition as claimed in claim 13, wherein:
in Formula 1A, $R_2$ and $R_3$ are combined with each other to form an aromatic ring represented by Formula A,

[Formula A]

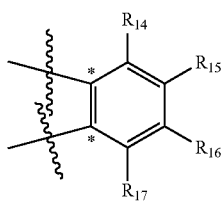

in Formula A, $R_{14}$, $R_{15}$, $R_{16}$ and $R_{17}$ are each independently hydrogen, a halogen, an alkyl group having 1 to 7 carbon atoms, a carbonyl group having 1 to 7 carbon atoms, an ester group having 1 to 7 carbon atoms, an acetal group having 1 to 7 carbon atoms, an alkoxy group having to 7 carbon atoms, or an ether group having 1 to 7 carbon atoms.

15. A composition, comprising:
a polymer;
a quencher; and
a photo-acid generator represented by Formula A-1,

[Formula A-1]

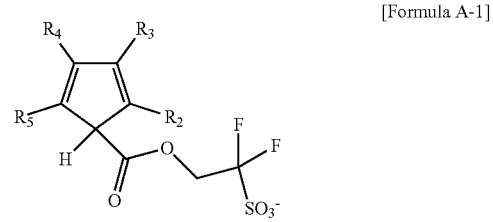

in Formula A-1, $R_2$, $R_3$, $R_4$ and $R_5$ are each independently hydrogen, a halogen, a substituted or unsubstituted alkyl group having 1 to 7 carbon atoms, a substituted or unsubstituted ester group having 1 to 7 carbon atoms, an acetal group having 1 to 7 carbon atoms, an alkoxy group having 1 to 7 carbon atoms, or an ether group having 1 to 7 carbon atoms; $R_2$, $R_3$, $R_4$ and $R_5$ being separate or adjacent ones thereof are combined to form an aromatic ring having 3 to 20 carbon atoms provided that the photo-acid generator represented by Formula A-1 is not the following compound:

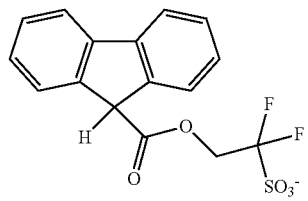

and
provided that when $R_2$ and $R_3$ of Formula A-1 are combined with each other to form an aromatic ring having 6 carbon atoms and $R_4$ and $R_5$ of Formula A-1 are combined with each other to form an aromatic ring having 6 carbon atoms, each aromatic ring having 6 carbon atoms is substituted with at least one of an ester group having 1 to 7 carbon atoms or an acetal group having 1 to 7 carbon atoms.

16. The composition as claimed in claim 15, wherein:
the photo-acid generator represented by Formula A-1 includes a compound represented by Formula 1-1, Formula 1-2, Formula 1-3, or Formula 1-4,

[Formula 1-1]

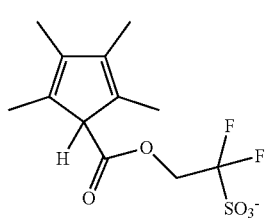

-continued

[Formula 1-2]

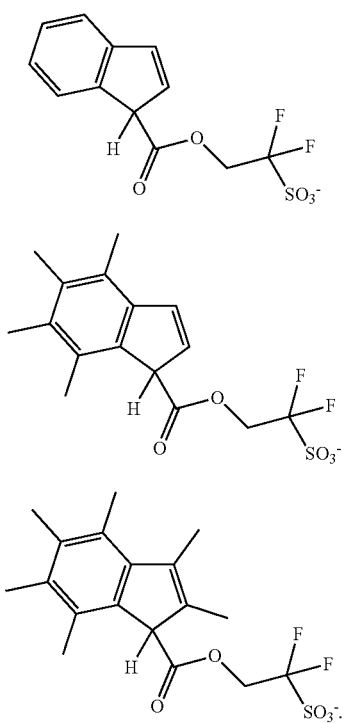

[Formula 1-3]

[Formula 1-4]

17. The composition as claimed in claim 15, wherein:
the photo-acid generator further includes a compound represented by Formula A-2 or Formula A-3,

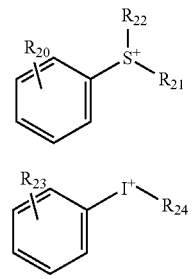

[Formula A-2]

[Formula A-3]

in Formula A-2,
$R_{20}$ is hydrogen, a halogen, or a substituted or unsubstituted alkyl group having 1 to 5 carbon atoms, and
$R_{21}$ and $R_{22}$ are each independently an alkyl group having 1 to 7 carbon atoms or a substituted or unsubstituted aromatic ring group having 4 to 20 carbon atoms,
in Formula A-3,
$R_{23}$ is hydrogen or a substituted or unsubstituted alkyl group having 1 to 5 carbon atoms, and
$R_{24}$ is an alkyl group having 1 to 7 carbon atoms or a substituted or unsubstituted aromatic ring group having 4 to 20 carbon atoms.

18. The composition as claimed in claim 17, wherein a number of equivalents of the compound represented by Formula A-1 is the same as a sum of equivalents of the compounds represented by Formula A-2 and Formula A-3 such that ions are balanced to form a charge neutral compound.

* * * * *